US007010981B1

(12) United States Patent
Hull (10) Patent No.: US 7,010,981 B1
(45) Date of Patent: Mar. 14, 2006

(54) INVERSE METHOD FOR ESTIMATING THE WAVE PROPAGATION PARAMETERS OF TWO DISSIMILAR WAVE TYPES

(75) Inventor: Andrew J. Hull, Newport, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 64 days.

(21) Appl. No.: 10/912,695

(22) Filed: Aug. 6, 2004

(51) Int. Cl.
*G01N 29/46* (2006.01)

(52) U.S. Cl. .......................... 73/602; 702/17; 702/39; 702/56; 702/103

(58) Field of Classification Search .................. 73/602
See application file for complete search history.

(56) References Cited

U.S. PATENT DOCUMENTS

| 4,321,981 | A | | 3/1982 | Waters |
| 4,907,670 | A | | 3/1990 | Anstey |
| 5,035,144 | A | * | 7/1991 | Aussel ....................... 73/602 |
| 5,127,268 | A | * | 7/1992 | Kline ......................... 73/597 |
| 5,251,486 | A | * | 10/1993 | Thompson et al. ........... 73/597 |
| 5,363,701 | A | | 11/1994 | Lee et al. |
| 5,495,763 | A | | 3/1996 | Rhodes et al. |
| 5,533,399 | A | | 7/1996 | Gibson et al. |
| 5,540,096 | A | * | 7/1996 | Woodcock et al. ........... 73/579 |
| 5,663,501 | A | | 9/1997 | Nakamura et al. |
| 6,006,163 | A | | 12/1999 | Lichtenwalner et al. |
| 6,205,859 | B1 | | 3/2001 | Kwun et al. |
| 6,766,252 | B1 | * | 7/2004 | Blanch et al. .................. 702/6 |
| 6,868,341 | B1 | * | 3/2005 | Valero ......................... 702/11 |

\* cited by examiner

*Primary Examiner*—Hezron Williams
*Assistant Examiner*—Rose M. Miller
(74) *Attorney, Agent, or Firm*—James M. Kasischke; Jean-Paul A. Nasser; Michael P. Stanley (57) ABSTRACT

A method is provided to distinguish two blended but different waves in a structure, such as compressional and shear waves, by measuring their corresponding wavenumbers and wave speeds. Other characteristics of the two waves may also be measured such as the propagation coefficients of both waves. All measurements can be calculated at every frequency for which a transfer function measurement is made. The measurements do not depend on the resonance frequencies of the structure and do not require curve fitting to the transfer functions.

10 Claims, 10 Drawing Sheets

INVERSE METHOD FOR ESTIMATING THE WAVE PROPAGATION PARAMETERS OF TWO DISSIMILAR WAVE TYPES

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates generally to determining wave propagation parameters and, more particularly, to determining wave propagation parameters of two dissimilar wave types that have been blended together.

(2) Description of the Prior Art

Measuring the wave propagation parameters of structures is important because these parameters significantly contribute to the static and dynamic response of the structures. Because most measurement methods are designed to isolate and measure one specific wave, they fail to correctly analyze dual wave propagation.

Resonant techniques have been used to identify and measure longitudinal properties for many years. These methods are based on comparing the measured eigenvalues of a structure to predicted eigenvalues from a model of the same structure. Resonant techniques only allow measurements at natural frequencies and do not have the ability to separate two different wave types propagating in a structure.

Comparison of analytical models to measured frequency response functions is another method that has been used to estimate stiffness and loss parameters of a structure. When the analytical model agrees with one or more frequency response functions, the parameters used to calculate the analytical model are considered accurate. If the analytical model is formulated using a numerical method, a comparison of the model to the data can be difficult due to dispersion properties of the materials. Additionally, many finite element algorithms have difficulty calculating responses of structures when there is a large mismatch in wavespeeds.

Previous efforts to solve problems related to the above are described by the following patents:

U.S. Pat. No. 4,321,981 issued Mar. 30, 1982, to K. H. Waters, discloses combination of fixed geometry of vibrating masses on a baseplate coupled to the ground, the masses being at a fixed angle to each other and of relatively variable phase, can be controlled to produce both compressional and shear waves simultaneously in a seismic exploration system.

U.S. Pat. No. 4,907,670, issued Mar. 13, 1990, to N. A. Anstey, discloses a method of seismic exploration using swept-frequency signals, compressional and shear waves are emitted simultaneously. Typically the waves are generated by swinging-weight vibrators acting through a single baseplate. If the frequency of the shear vibration is one-half that of the compressional vibration, the downward vertical forces can be phased to minimize the horizontal slippage of the baseplate. The sensitive axis of the geophones is inclined to the vertical for detecting both compressional waves and shear waves. For defined ranges of sweep rate, separate compressional and shear records are obtained by cross-correlating the geophone signal separately against the vertical and horizontal emissions.

U.S. Pat. No. 5,363,701, issued Nov. 15, 1994, to Lee et al., discloses a plurality of elongated test specimens undergo vibrations induced by ran noise within an acoustical frequency range establishing standing waves therein having resonant frequencies at which the collection of measurement data through accelerometers mounted at the ends of the specimens provides for calculation of physical material properties. The processing of the data during collection, analysis and calculation is automated by programmed computer control.

U.S. Pat. No. 5,533,399, issued Jul. 9, 1996, to Gibson et al., discloses a method and apparatus for deriving four independent elastic constants (longitudinal and transverse. Young's moduli, in-plane shear modulus and major Poisson's ratio) of composite materials from the modal resonance data of a freely-supported rectangular thin plate made from the material. The method includes the steps of: suspending a panel of the material from a rigid support by a plurality of filaments having a low support stiffness which has minimal effect on motion of the panel; providing a vibration sensor to detect a vibration response in the panel; imparting an impulse to the panel; generating a response signal proportionate to the response in the panel to the impulse imparted; generating an excitation signal in proportion to the impulse; communicating the signals to an analyzer for transforming the signals into a frequency domain; deriving resonance frequencies and associated mode shape indices of the panel; communicating the resonance frequencies and the mode shape indices to a computing device; and predicting and displaying the elastic constants using the computing device.

U.S. Pat. No. 5,663,501, issued Sep. 2, 1997, to Nakamura et al., discloses a vibration sensor is placed on each of the top surface of a layer of the structure and the ground surface near the structure so as to record vibrations. A seismic vulnerability data processor assumes a transfer function of vibration of the top surface of the layer of the structure based on a spectral ratio between the vibration recorded on the top surface of the layer of the structure and the vibration recorded on the ground surface, thereby obtaining a predominant frequency and amplification factor of vibration of the top surface of the layer of the structure. A seismic vulnerability index of the layer of the structure resulting from a deformation of the layer is obtained based on the obtained predominant frequency and amplification factor of vibration of the top surface of the layer of the structure and on the height of the layer of the structure. This seismic vulnerability index is multiplied by an assumed seismic acceleration so as to obtain a maximum shear strain of the layer of the structure upon being subjected to an earthquake.

U.S. Pat. No. 6,006,163, issued Dec. 21, 1999, to Lichtenwalner et al., discloses a An active damage interrogation (ADI) system (and method) which utilizes an array of piezoelectric transducers attached to or embedded within the structure for both actuation and sensing. The ADI system actively interrogates the structure through broadband excitation of the transducers. The transducer (sensor) signals are digitized and the transfer function of each actuator/sensor pair is computed. The ADI system compares the computed transfer function magnitude and phase spectrum for each actuator/sensor pair to a baseline transfer function for that actuator/sensor pair which is computed by averaging several sets of data obtained with the structure in an undamaged state. The difference between the current transfer function and the baseline transfer function for each actuator/sensor pair is normalized by the standard deviation associated with that baseline transfer function. The transfer function deviation for each actuator/sensor pair is then represented in terms of the number of standard deviations, or sigmas, from the baseline. This statistic, termed the TF Delta, is then processed by a windowed local averaging function in order to reduce minor variations due to random noise, etc. The Windowed TF Delta for each actuator/sensor pair is then integrated over the entire excitation frequency spectrum, to thereby produce the Cumulative Average Delta, which provides a single metric for assessing the magnitude of change (deviation from baseline) of that particular actuator/sensor transfer function. The Cumulative Average Delta (CAD) for each actuator/sensor transfer function provides key, first-level information which is required for detecting, localizing, and quantitatively assessing damage to the structure.

U.S. Pat. No. 6,205,859 B1, issued Mar. 27, 2001, to Kwun et al., discloses an improved method for defect detection with systems using magnetostrictive sensor techniques. The improved method involves exciting the magnetostrictive sensor transmitter by using a relatively broadband signal instead of a narrow band signal typically employed in existing procedures in order to avoid signal dispersion effects. The signal detected by the magnetostrictive sensor receiver is amplified with an equally broadband signal amplifier. The amplified signal is transformed using a time-frequency transformation technique such as a short-time Fourier transform. Finally, the signal characteristics associated with defects and anomalies of interest are distinguished from extraneous signal components associated with known wave propagation characteristics. The process of distinguishing defects is accomplished by identifying patterns in the transformed data that are specifically oriented with respect to the frequency axis for the plotted signal data. These identified patterns correspond to signals from either defects or from known geometric features in the pipe such as welds or junctions. The method takes advantage of a priori knowledge of detected signal characteristics associated with other wave modes (such as flexural waves) and sensor excitation as well the effects caused by liquid induced dispersion.

U.S. Pat. No. 4,418,573, issued Dec. 6, 1983, to Madigosky et al., discloses a fast and reliable method is disclosed for measuring the dynamic mechanical properties of a material, particularly its modulus of elasticity and loss factor. By this method the acoustic characteristics of a material can be determined. An elongate strip of material, whose properties are desired to be known, is provided with miniature accelerometers fixedly secured to its opposite ends. One end of the strip is excited by a random noise source which travels toward the other end where that end and accelerometer is allowed to move freely (unrestrained). The accelerometers measure the ratios of acceleration at two locations over an extended frequency range of 0.2 Hz to 25 KHz, and the information is processed through a fast Fourier transform spectrum analyzer for determining amplitude of acceleration ratio and phase difference between the two accelerometers from which Young's modulus and loss factor for that material are determined.

The above listed patents and other prior art do not provide for a method for estimating wave propagation parameters of two dissimilar wave type that have been blended together. More specifically the above listed prior art does not disclose methods for determining system response to different types of wave motion (e.g. compressional and shear wave motion) characterized using wave numbers, wavespeeds, and wave propagation coefficients which are determined/estimated based on measurements at various positions in the media using suitable sensors, e.g., accelerometers. Suitable measurements might comprise one or more measurements of strain, velocity, acceleration, or displacement.

Consequently, those skilled in the art will appreciate the present invention that addresses the above and other problems.

SUMMARY OF THE INVENTION

An object of the present invention is a method to separate and measure the characteristics of two dissimilar waves propagating in a finite or infinite space.

These and other objects, features, and advantages of the present invention will become apparent from the drawings, the descriptions given herein, and the appended claims. However, it will be understood that above listed objects and advantages of the invention are intended only as an aid in understanding aspects of the invention, are not intended to limit the invention in any way, and do not form a comprehensive list of objects, features, and advantages.

Accordingly, the present invention provides a method for characterizing the system response of a structure. The method comprises one or more steps such as, for instance, vibrating the structure in a manner that simultaneously excites a first wave and a second wave such that the first wave and the second wave comprise different types of wave motion. Other steps comprise making seven movement related measurements in the structure at seven different positions in the structure and setting the seven movement related measurements equal to seven frequency domain transfer functions. The seven frequency domain transfer functions are described in terms of six unknowns. The six unknowns comprise two unknowns related to a complex wavenumber for each of the first wave and the second wave and four unknowns related to four wave propagation coefficients for the first wave and the second wave. Other steps comprise determining a complex wavenumber for each of the first wave and the second wave utilizing the equations described herein. The method further comprises determining a wavespeed for the first wave and the second wave from the complex wavenumber for each of the first wave and the second wave. Other steps comprise utilizing matrix to solve for the four unknowns related to the wave propagation coefficients for the first wave and the second wave.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawing, wherein the figures graphically show the results of a numerical example of the method and wherein.

DESCRIPTION OF THE PREFERRED EMBODIMENT

The present invention provides a method to separate and measure the characteristics of two dissimilar waves propagating in a finite or infinite media. This method is particularly useful in steady state measurement processes where both waves are "blended" together in the measurement data. Additionally, it is applicable to structures with finite spatial lengths whose boundaries produce reflected wave energy that is difficult to model. A typical system is a structure that supports a longitudinal and a shear wave traveling in both directions across its media. The present invention provides the ability to separate two different waves and measure their corresponding wavenumbers and wavespeeds on a finite or infinite media. As well, the present invention provides the ability to measure propagation coefficients for each wave. Additionally, all measurements can be calculated at every frequency that a transfer function measurement is made. They do not depend on system resonant frequencies or curve fitting to transfer functions. The calculation from transfer function measurement to calculation of all system parameters is exact, i.e., no errors are introduced during this process.

The present method preferably uses seven transfer functions that are obtained by vibrating the structure in a method that excites two different types of wave motion. Measurements may be made of either strain, displacement, velocity, or acceleration of the structure. Once this is accomplished, the seven measurements are combined to yield a closed form solution of both wavenumbers and wavespeeds. The four corresponding wave propagation coefficients are also estimated with a closed form solution during this process. Once these six parameters are known, the system response can be correctly characterized.

The present invention provides an inverse method to separate and measure complex wavenumbers, wavespeeds, and the corresponding wave propagation coefficients of a media that supports two different wave motions. This approach is intended for use when a structure is to undergo motion that will produce two dissimilar waves. This system typically arises in cars, ships, aircraft, bridges, buildings, earth, and biological tissue. Frequently, these systems support compressional wave and shear wave propagation simultaneously. The present invention begins with two wave equations of motion and the resulting solutions added together. An inverse method is developed using seven transfer function measurements that are combined to yield closed form values of wavenumbers, wavespeeds, and wave propagation coefficients at any given test frequency.

The system model provides that two different waves are traveling in a media, both of which can be independently modeled using the wave equation, written as $$\frac{\partial^2 u_1(x,t)}{\partial t^2} - c_1^2 \frac{\partial^2 u_1(x,t)}{\partial x} = 0. \tag{1}$$

and $$\frac{\partial^2 u_2(x,t)}{\partial t^2} - c_2^2 \frac{\partial^2 u_2(x,t)}{\partial x} = 0. \tag{2}$$

where x is the distance along the media (m), t is time (s), u is a field variable of the media, c is the complex wavespeed (m/s), and the subscripts one and two correspond to the first and second waves, respectively. The wavespeeds may be a function of frequency, which is behavior that corresponds to many mechanical systems. The field variable is typically some measurable quantity such as displacement, velocity, acceleration, pressure, or strain. The field variable is modeled as a steady state response in frequency and is expressed as $$u_1(x,t) = U_1(x,\omega) \exp(i\omega t), \tag{3}$$

and $$u_2(x,t) = U_2(x,\omega) \exp(i\omega t), \tag{4}$$

where $\omega$ is the frequency of excitation (rad/s), $U(x, \omega)$ is the temporal Fourier transform of the field variable, and i is the square root of $-1$. The temporal solution to equations (1) and (2), derived using equations (3) and (4), written in terms of trigonometric functions, and using the principal of superposition, is $$\begin{aligned} U(x,\omega) &= U_1(x,\omega) + U_2(x,\omega) \\ &= A(\omega)\cos[k(\omega)x] + B(\omega)\sin[k(\omega)x] + \\ &\quad C(\omega)\cos[p(\omega)x] + D(\omega)\sin[p(\omega)x], \end{aligned} \tag{5}$$

where $A(\omega)$, $B(\omega)$, $C(\omega)$, and $D(\omega)$ are wave propagation coefficients and $k(\omega)$ and $p(\omega)$ are the complex wave numbers given by:

$$k(\omega) = \frac{\omega}{c_1}. \tag{6}$$

and $$p(\omega) = \frac{\omega}{c_2}. \tag{7}$$

Without loss of generality, it is assumed that $abs(c_1) > abs(c_2)$ which also corresponds to $abs[k(\omega)] < abs[p(\omega)]$. For brevity, the $\omega$ dependence is omitted from the wave propagation coefficients and the wavenumbers during the remainder of this discourse. Note that equations (1) and (2) are independent of boundary conditions, and the inverse model developed in the next section does not need boundary condition or structural load specifications to estimate the model parameters.

Equation (5) has six unknowns and is nonlinear with respect to the unknown wavenumbers k and p. It will be shown that using seven independent, equally spaced measurements, that the six unknowns can be estimated with closed form solutions. Seven frequency domain transfer functions of the field variable are now measured. These consist of the measurement at some location divided by a common reference measurement. Typically, this would be an accelerometer at a measurement location on the structure and an accelerometer at some other location on the structure. The first accelerometer changes position for each measurement and the second accelerometer's position is fixed. These seven measurements are set equal the theoretical expression given in equation (5) and are $$T_{-3} = \tag{8}$$
$$\frac{U_{-3}(-3\delta, \omega)}{V_0(\omega)} = A\cos(3k\delta) - B\sin(3k\delta) + C\cos(3p\delta) - D\sin(3p\delta),$$

$$T_{-2} = \tag{9}$$
$$\frac{U_{-2}(-2\delta, \omega)}{V_0(\omega)} = A\cos(2k\delta) - B\sin(2k\delta) + C\cos(2p\delta) - D\sin(2p\delta),$$

$$T_{-1} = \frac{U_{-1}(-\delta, \omega)}{V_0(\omega)} = A\cos(k\delta) - B\sin(k\delta) + C\cos(p\delta) - D\sin(p\delta), \tag{10}$$

$$T_0 = \frac{U_0(0, \omega)}{V_0(\omega)} = A + C, \tag{11}$$

$$T_1 = \frac{U_1(\delta, \omega)}{V_0(\omega)} = A\cos(k\delta) + B\sin(k\delta) + C\cos(p\delta) + D\sin(p\delta), \tag{12}$$

$$T_2 = \frac{U_2(2\delta, \omega)}{V_0(\omega)} = A\cos(2k\delta) + B\sin(2k\delta) + C\cos(2p\delta) + D\sin(2p\delta), \tag{13}$$

and $$T_3 = \frac{U_3(2\delta, \omega)}{V_0(\omega)} = A\cos(3k\delta) + B\sin(3k\delta) + C\cos(3p\delta) + D\sin(3p\delta), \tag{14}$$

where $\delta$ is the sensor to sensor separation distance (m) and $V_0(\omega)$ is the reference measurement. Note that the units of the transfer functions given in equations (8)–(14) dimensionless if the reference measurement has units that are the same as the field measurements.

Equation (10) is now subtracted from equation (12), equation (9) is now subtracted from equation (13), and equation (8) is subtracted from equation (14), yielding the following three equations.

$$B\sin(k\delta) + D\sin(p\delta) = \frac{T_1 - T_{-1}}{2}, \tag{15}$$

$$B\sin(2k\delta) + D\sin(2p\delta) = \frac{T_2 - T_{-2}}{2}, \tag{16}$$

and $$B\sin(3k\delta) + D\sin(3p\delta) = \frac{T_3 - T_{-3}}{2}. \tag{17}$$

Equations (15), (16), and, (17) are now combined and simplified using multi-angle trigonometric relationships to give $$\cos(k\delta)\cos(p\delta) + \tag{18}$$
$$\left[\frac{T_2 - T_{-2}}{2(T_1 - T_{-1})}\right][\cos(k\delta) + \cos(p\delta)] + \left[\frac{T_3 - T_{-3} + T_i - T_{-1}}{4(T_1 - T_{-1})}\right] = 0.$$

Equation (10) is now added to equation (12) and equation (9) is added to equation (13), yielding the following two equations:

$$A\cos(k\delta) + C\cos(p\delta) = \frac{T_1 - T_{-1}}{2}, \tag{19}$$

and $$A\cos(k\delta) + C\cos(p\delta) = \frac{T_2 - T_{-2}}{2}. \tag{20}$$

Equations (11), (19), and (2) are now combined and simplified using multi-angle trigonometric relationships to yield $$\cos(k\delta)\cos(p\delta) + \tag{21}$$
$$\left[\frac{T_1 - T_{-2}}{2(T_0)}\right][\cos(k\delta) + \cos(p\delta)] + \left[\frac{T_2 - T_{-2} + 2T_0}{4T_0}\right] = 0.$$

Equations (18) and (21) are now combined, and the result is a binomial expression with respect to the cosine function with either $k\delta$ or $p\delta$ as an argument. This is written as $$a\cos^2\left[\binom{k}{p}\delta\right] + b\cos\left[\binom{k}{p}\delta\right] + c = 0. \tag{22}$$

where $$a = 4T_1^2 - 4T_{-1}^2 + 4T_{-2}T_0 - 4T_0T_2, \tag{23}$$

$$b = 2T_{-2}T_{-1} - 2T_{-2}T_1 + 2T_{-1}T_0 - 2T_0T_1 + 2T_{-1}T_2 - 2T_1T_2 + 2T_0T_3 - 2T_{-3}T_0, \tag{24}$$

and $$c = T_{-1}^2 - T_1^2 + T_2^2 - T_{-2}^2 + T_{-3}T_{-1} - T_{-1}T_3 + T_{-3}T_1 - T_1T_3 + 2T_0T_2 - 2T_{-2}T_0. \tag{25}$$

Equation 22 is now solved using $$\cos\left[\binom{k}{p}\delta\right] = \frac{-b \pm \sqrt{b^2 - 4ac}}{2a} = \phi, \tag{26}$$

where $\phi$ is typically a complex number. Equation (26) is two solutions to equation (22), which is further separated by writing it as $$\cos(g\delta) = \frac{-b + \sqrt{b^2 - 4ac}}{2a} = \phi_p, \tag{27}$$

-continued $$\cos(h\delta) = \frac{-b - \sqrt{b^2 - 4ac}}{2a} = \phi_m, \quad (28)$$

where g and h are wavenumbers that are equal to k and p (not necessarily respectively).

The relationship between g, h, k, and p is now discussed. This begins by defining two functions from equations (27) and (28). They are $$s_p = [\text{Re}(\phi_p)]^2 + [\text{Im}(\phi_p)]^2 - \sqrt{\{[\text{Re}(\phi_p)]^2 + [\text{Im}(\phi_p)]^2\}^2 - \{2[\text{Re}(\phi_p)]^2 - 2[\text{Im}(\phi_p)]^2 - 1\}}, \quad (29)$$

and $$s_m = [\text{Re}(\phi_m)]^2 + [\text{Im}(\phi_m)]^2 - \sqrt{\{[\text{Re}(\phi_m)]^2 + [\text{Im}(\phi_m)]^2\}^2 - \{2[\text{Re}(\phi_m)]^2 - 2[\text{Im}(\phi_m)]^2 - 1\}}, \quad (30)$$

These functions, along with the function $$\theta = \text{angle}(b^2 - 4ac), \quad (31)$$

are used to determine the wavenumber relationships. At zero frequency, equations (27) and (29), which contain the positive values of $\phi$, correspond to the slower wave (or the higher wavenumber); in this case the wave associated with wavespeed $C_2$ and wavenumber p. Or in other words, at zero (and low) frequency, p=g. Conversely, at zero frequency, equations (28) and (30), which contains the negative values of $\phi$, correspond to the faster wave (or lower wavenumber), in this case the wave associated with wavespeed $c_1$ and wavenumber k. Or in other words, at zero (and low 0 frequency, k=h. Every time $\theta$ (from equation (31)) cycles through $2\pi$ revolutions, the relationship between p and k interchanges. This can be stated in equation form as $$(2j-1)\pi < \theta < (2j+1)\pi \quad j = 0, 2, 4, 6 \ldots \quad \begin{cases} p = g \\ k = h \end{cases}, \text{ and} \quad (32)$$

$$(2j-1)\pi < \theta < (2j+1)\pi \quad j = 1, 3, 5, 7 \ldots \quad \begin{cases} p = h \\ k = g \end{cases}, \quad (33)$$

where j is the wrap counting integer. The wavenumbers are now determined based on equations (32) and (33).

If equation (32) is satisfied, then the solution to the real part of p is $$\text{Re}(p) = \begin{cases} \frac{1}{2\delta}\text{Arccos}(s_p) + \frac{n\pi}{2\delta} & n \text{ even} \\ \frac{1}{2\delta}\text{Arccos}(-s_p) + \frac{n\pi}{2\delta} & n \text{ odd} \end{cases}, \quad (34)$$

and the capital A denotes the principal value of the inverse cosine function. The value of n is determined from the function $s_p$, which is a periodically varying cosine function with respect to frequency. At zero frequency, n is 0. Every time $s_p$ cycles through $\pi$ radians (180 degrees), n is increased by 1. When the solution to the real part of p is found, the solution to the imaginary part of p is then written as $$\text{Im}(p) = \frac{1}{\delta}\log_e\left[\frac{\text{Re}(\phi_p)}{\cos[\text{Re}(p)\delta]} - \frac{\text{Im}(\phi_p)}{\sin[\text{Re}(p)\delta]}\right], \quad (35)$$

Additionally, the solution to the real part of k is $$\text{Re}(k) = \begin{cases} \frac{1}{2\delta}\text{Arccos}(s_m) + \frac{m\pi}{2\delta} & m \text{ even} \\ \frac{1}{2\delta}\text{Arccos}(-s_m) + \frac{m\pi}{2\delta} & m \text{ odd} \end{cases}, \quad (36)$$

The value of m is determined from the function $s_m$, which is a periodically varying cosine function with respect to frequency. At zero frequency, m is 0. Every time $s_m$ cycles through $\pi$ radians (180 degrees), m is increased by 1. When the solution to the real part of k is found, the solution to the imaginary part of k is then written as $$\text{Im}(k) = \frac{1}{\delta}\log_e\left[\frac{\text{Re}(\phi_m)}{\cos[\text{Re}(k)\delta]} - \frac{\text{Im}(\phi_m)}{\sin[\text{Re}(k)\delta]}\right]. \quad (37)$$

If equation (33) is satisfied, then the solution to the real part of p is $$\text{Re}(p) = \begin{cases} \frac{1}{2\delta}\text{Arccos}(s_m) + \frac{n\pi}{2\delta} & n \text{ even} \\ \frac{1}{2\delta}\text{Arccos}(-s_m) + \frac{n\pi}{2\delta} & n \text{ odd} \end{cases}, \quad (38)$$

and the capital A denotes the principal value of the inverse cosine function. The value of n is determined from the function $s_m$, which is a periodically varying cosine function with respect to frequency. At zero frequency, n is 0. Every time $s_m$ cycles through $\pi$ radians (180 degrees), n is increased by 1. When the solution to the real part of p is found, the solution to the imaginary part of p is then written as $$\text{Im}(p) = \frac{1}{\delta}\log_e\left[\frac{\text{Re}(\phi_m)}{\cos[\text{Re}(p)\delta]} - \frac{\text{Im}(\phi_m)}{\sin[\text{Re}(p)\delta]}\right]. \quad (39)$$

Additionally, the solution to the real part of k is $$\text{Re}(k) = \begin{cases} \frac{1}{2\delta}\text{Arccos}(s_m) + \frac{m\pi}{2\delta} & m \text{ even} \\ \frac{1}{2\delta}\text{Arccos}(-s_m) + \frac{m\pi}{2\delta} & m \text{ odd} \end{cases}. \quad (40)$$

The value of m is determined from the function $s_m$, which is a periodically varying cosine function with respect to frequency. At zero frequency, m is 0. Every time $s_m$ cycles through $\pi$ radians (180 degrees), m is increased by 1. When the solution to the real part of k is found, the solution to the imaginary part of k is then written as $$\text{Im}(k) = \frac{1}{\delta}\log_e\left[\frac{\text{Re}(\phi_m)}{\cos[\text{Re}(k)\delta]} - \frac{\text{Im}(\phi_m)}{\sin[\text{Re}(k)\delta]}\right]. \quad (41)$$

Once the wavenumbers have been determined, the wavespeeds at each frequency can be computed using $$c_1(\omega) = \frac{\omega}{k(\omega)}. \quad \text{and} \quad (42)$$

$$c_2(\omega) = \frac{\omega}{p(\omega)}. \quad (43)$$

The wave propagation coefficients can now be estimated by applying an ordinary least square fit to all the data points. This begins by formulating the problem using N (=7) algebraic equations where N is the number of sensors. Written in matrix form, they are $$Ax = b \quad \text{where} \quad (44)$$

$$A = \begin{bmatrix} \cos(3k\delta) & -\sin(3k\delta) & \cos(3p\delta) & -\sin(3p\delta) \\ \cos(2k\delta) & -\sin(2k\delta) & \cos(2p\delta) & -\sin(2p\delta) \\ \cos(k\delta) & -\sin(k\delta) & \cos(p\delta) & -\sin(p\delta) \\ 1 & 0 & 1 & 0 \\ \cos(k\delta) & \sin(k\delta) & \cos(p\delta) & \sin(p\delta) \\ \cos(2k\delta) & \sin(2k\delta) & \cos(2p\delta) & \sin(2p\delta) \\ \cos(3k\delta) & \sin(3k\delta) & \cos(3p\delta) & \sin(3p\delta) \end{bmatrix}, \quad (45)$$

$$x = \begin{bmatrix} A \\ B \\ C \\ D \end{bmatrix}, \quad (46)$$

$$b = \begin{bmatrix} T_{-3} \\ T_{-2} \\ T_{-1} \\ T_0 \\ T_1 \\ T_2 \\ T_3 \end{bmatrix}. \quad (47)$$

The solution to equation (44) is $$x = (A^H A)^{-1} A^H b, \quad (48)$$

where the superscript H denotes complex conjugate transpose of the matrix. It is noted that the above procedure of estimating wavenumbers and wave propagation coefficients from the data is a series of closed form equations.

Figure 1:
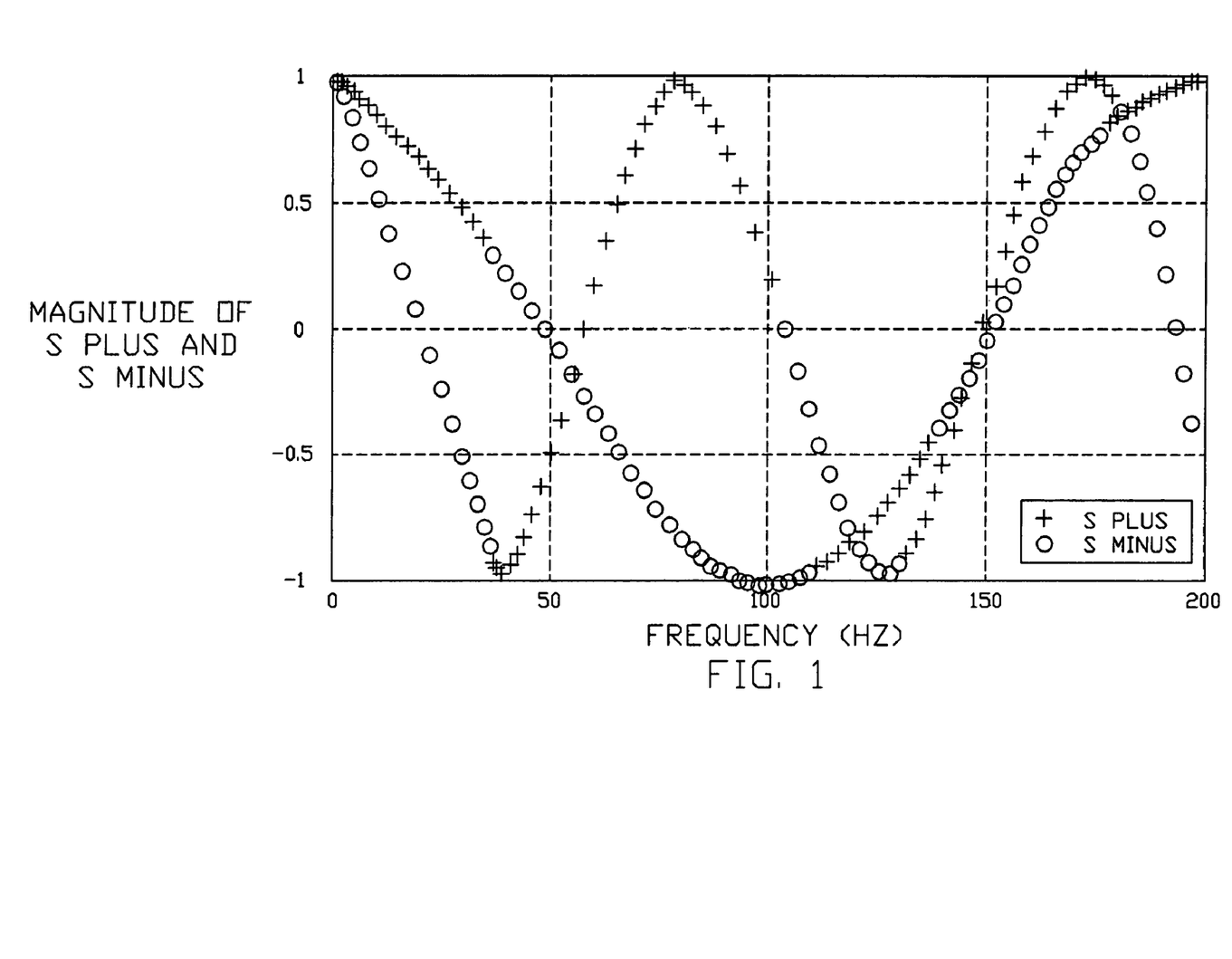
FIG. 1 is a plot of the functions $s_p$ (s plus) and $s_m$ (s minus) from equations (29) and (30), discussed hereinafter, respectively, versus frequency utilizing a numerical example of the method.
Figure 2:
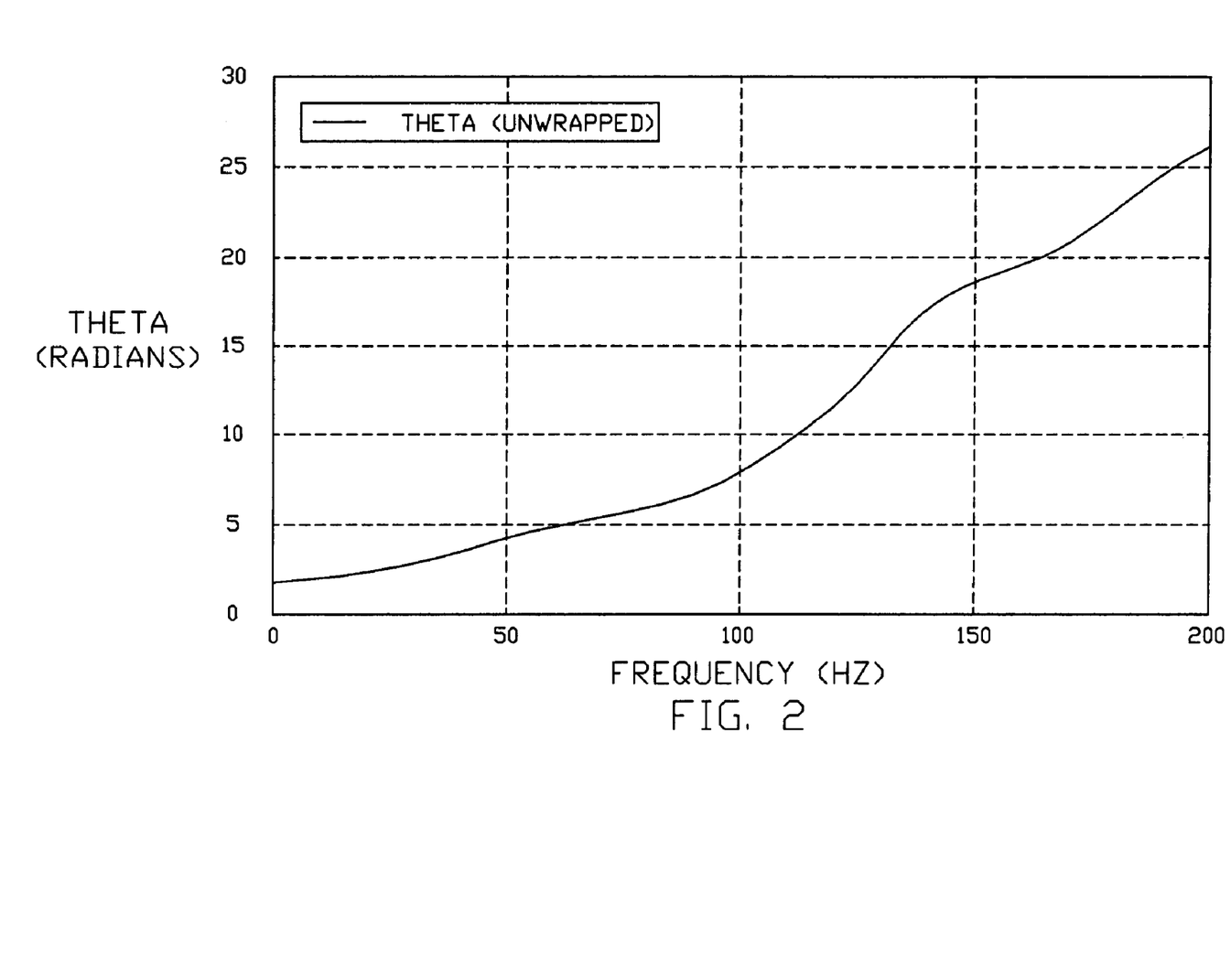
FIG. 2 is a plot of the unwrapped function θ from equation (31), discussed hereinafter, versus frequency.
Figure 3:
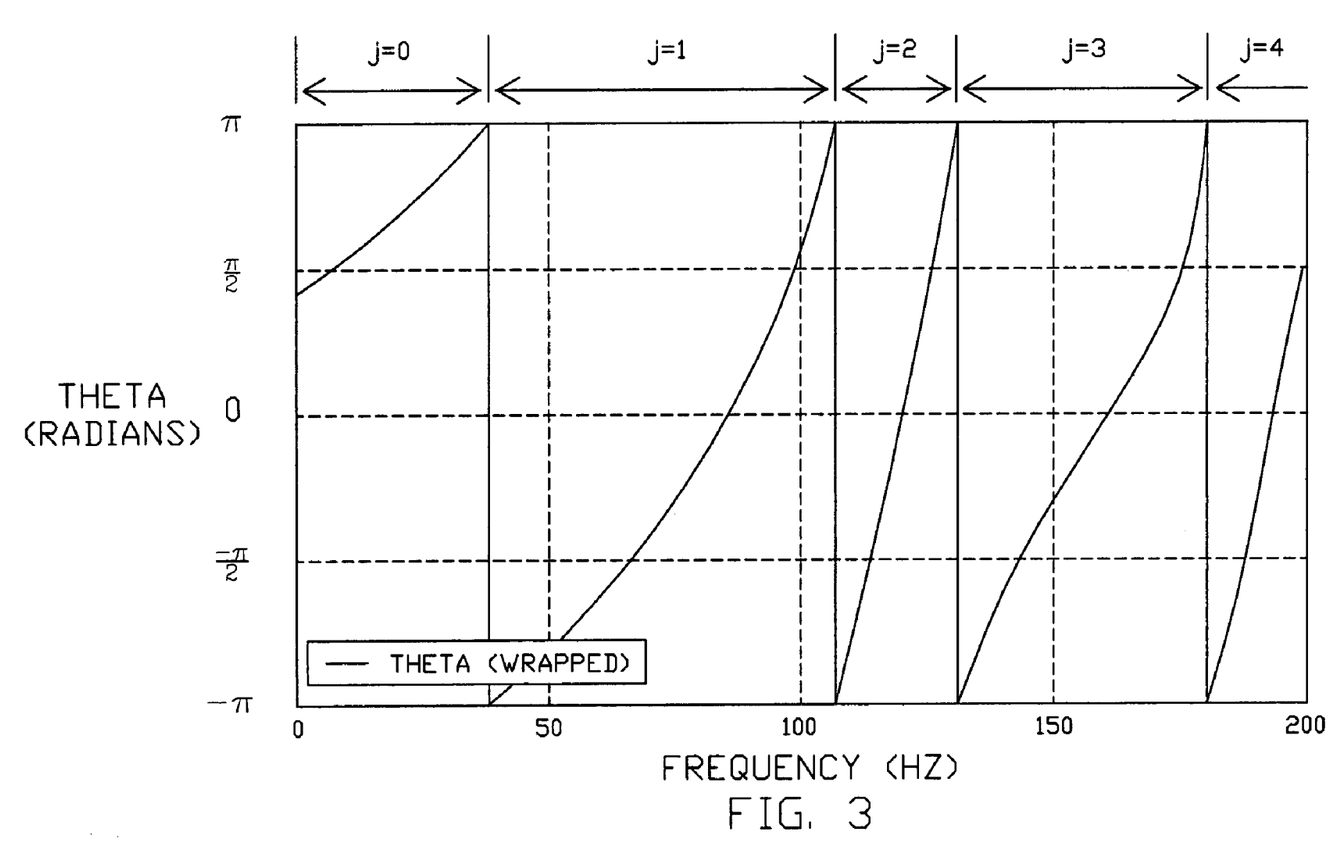
FIG. 3 is a plot of the function θ where the function is wrapped and the wrap counting integer j is denoted at the top of the plot.
Figure 4:
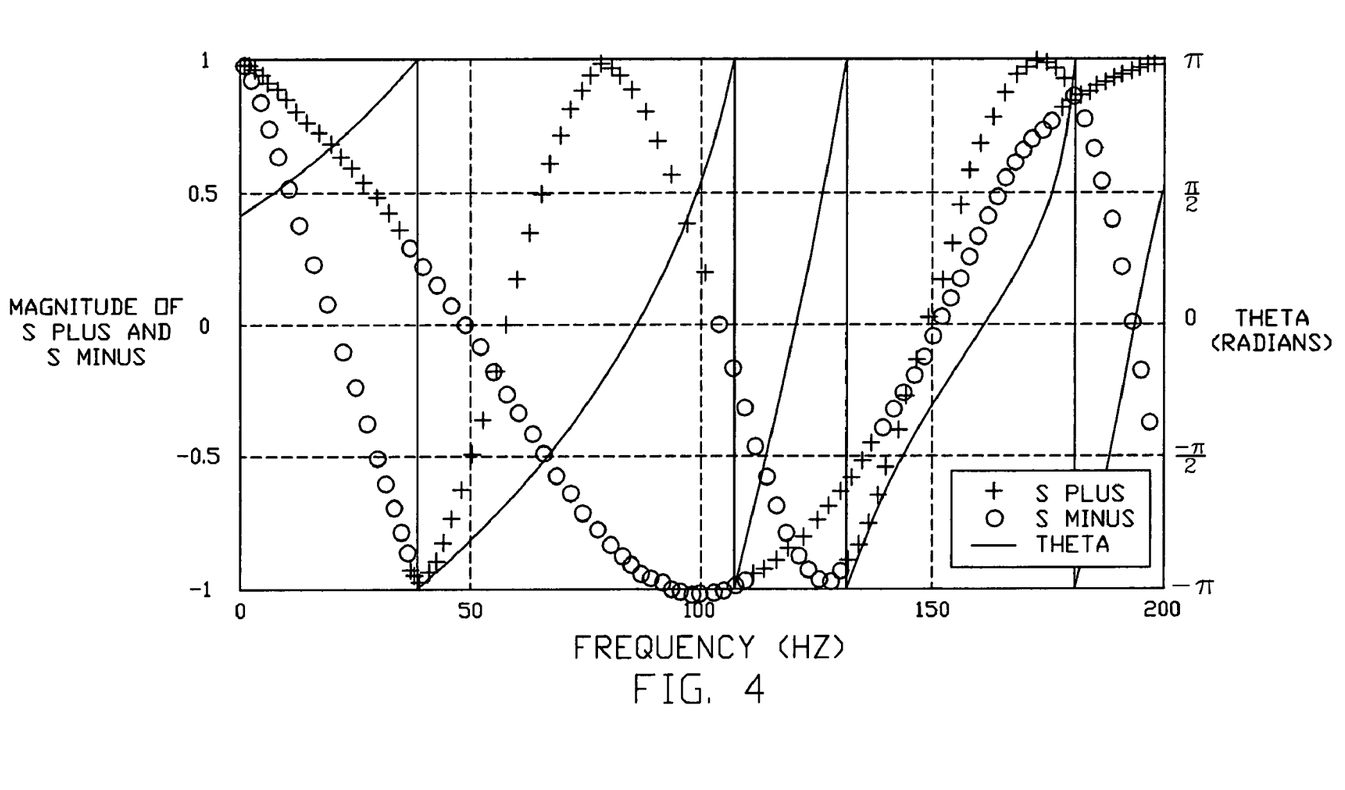
FIG. 4 is a plot of $s_p$, $s_m$, and (wrapped) θ displayed simultaneously which depicts the interchange relationship between the three functions.

A numerical example is developed to illustrate the method. The following parameters are used: $c_1$=230+20i, $c_2$=100+15i, d=0.6, A=5.2+8.1i, B=3.1+0.01ω, C=6.8+001ω, and D=2.1 where ω is frequency in rad/s and i is the square root of −1. Seven transfer functions were assembled using equations (8)–(14) and the constants listed above. The left-hand side of these equations (or the data) was processed according to equations (21)–(48). FIG. 1 is a plot of the functions $s_p$ (s plus) and $s_m$ (s minus) form equations (29) and (30), respectively, versus frequency. In FIG. 1, the function sp is denoted with a "+" sign and the functions $s_m$ is denoted with an "o" sign. FIG. 2 is a plot of the unwrapped function θ from equation (31) versus frequency. A better method of displaying θ is shown in FIG. 3, where the function is wrapped and the wrap counting integer j is denoted at the top of the plot. FIG. 4 is a plot of $s_p$, $s_m$, and (wrapped) θ displayed simultaneously which depicts the interchange relationship between the three functions. The sinusoidal half period counters n and m are determined by inspection of FIG. 4 and are listed in Tables 1 and 2.

Figure 5A:
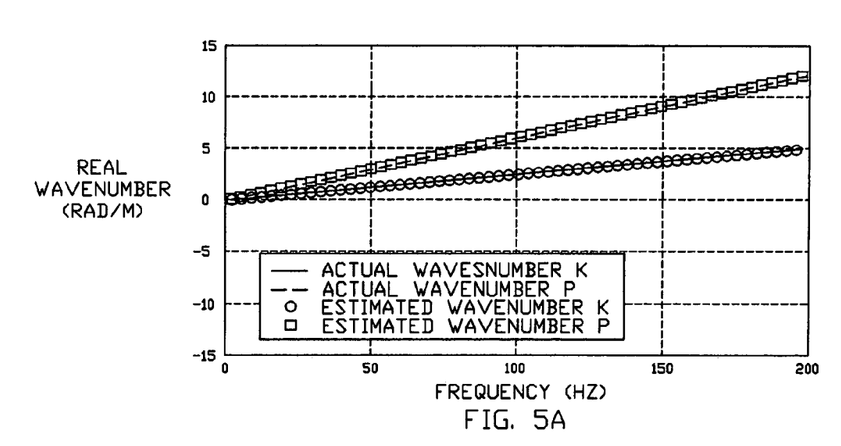
FIG. 5A is a plot of the real part of the wavenumbers versus frequency.
Figure 5B:
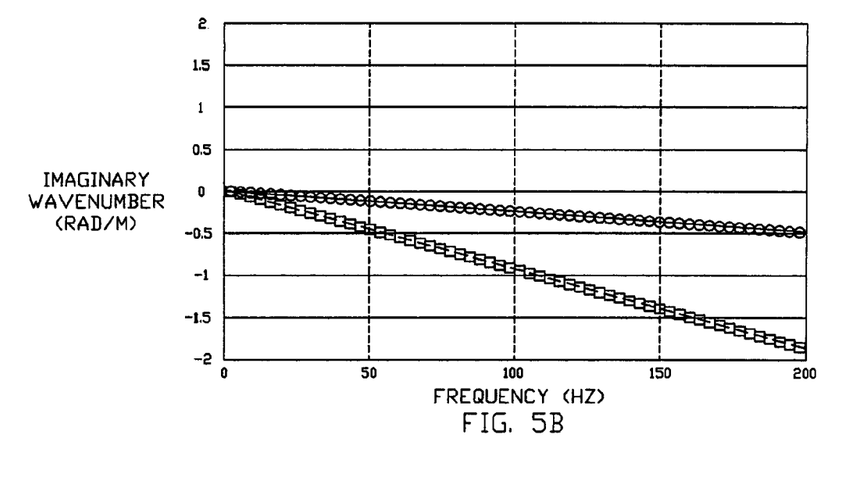
FIG. 5B is a plot of the imaginary part of the wavenumbers versus frequency.
Figure 6A:
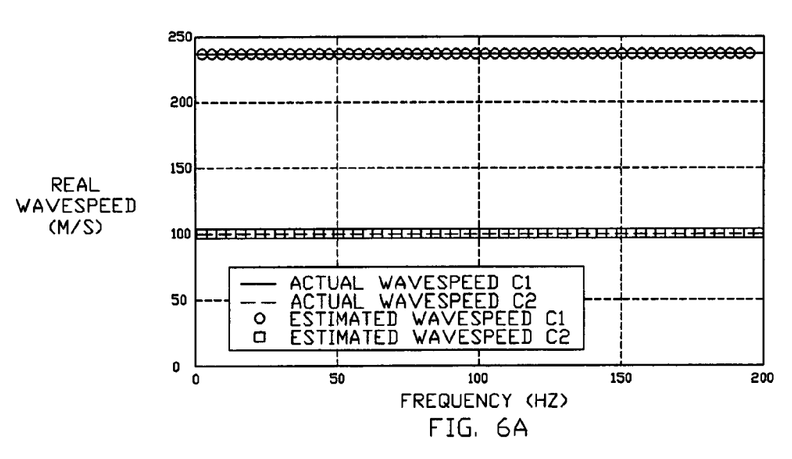
FIG. 6A is a plot of the real wavespeeds versus frequency.
Figure 6B:
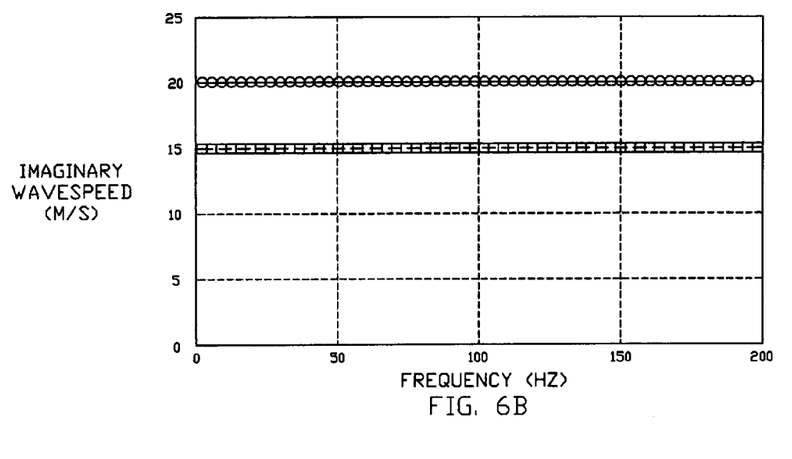
FIG. 6B is a plot of the imaginary wavespeeds versus frequency.
Figure 7A:
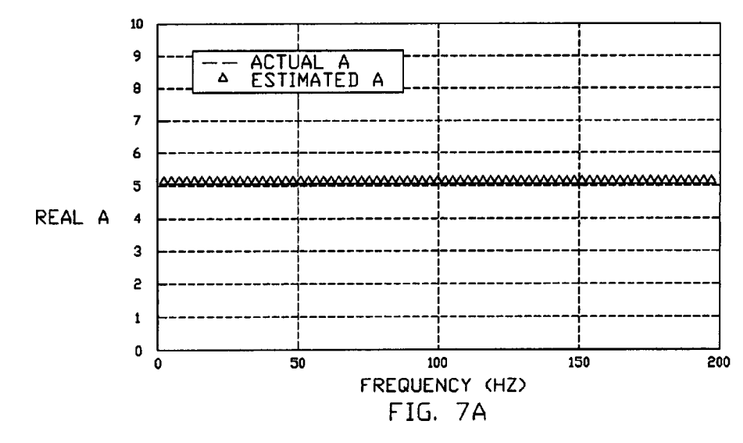
FIG. 7A is a plot of the real part of the wave propagation coefficient A versus frequency.
Figure 7B:
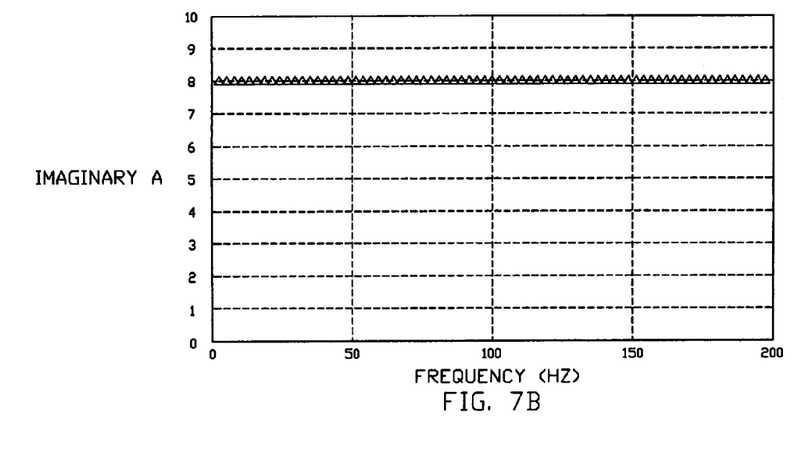
FIG. 7B is a plot of the imaginary part of the wave propagation coefficient A versus frequency
Figure 8A:
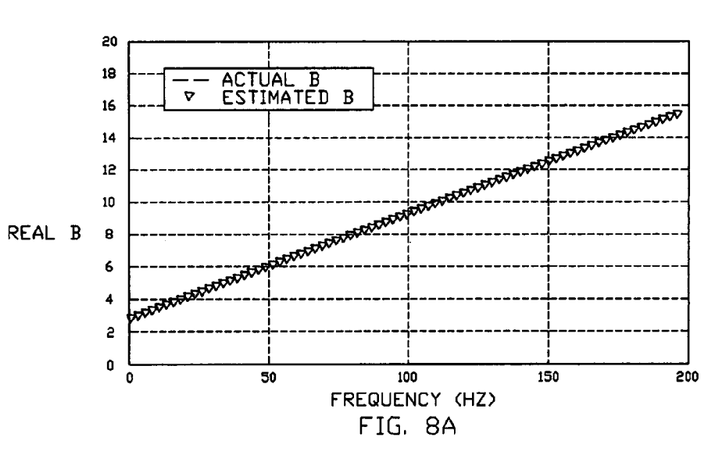
FIG. 8A is a plot of the real part of the wave propagation coefficient B versus frequency.
Figure 8B:
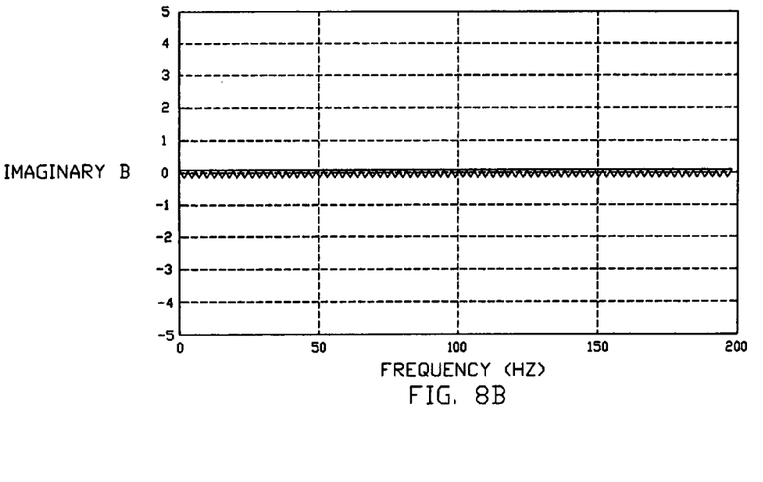
FIG. 8B is a plot of the imaginary part of the wave propagation coefficient B versus frequency.
Figure 9A:
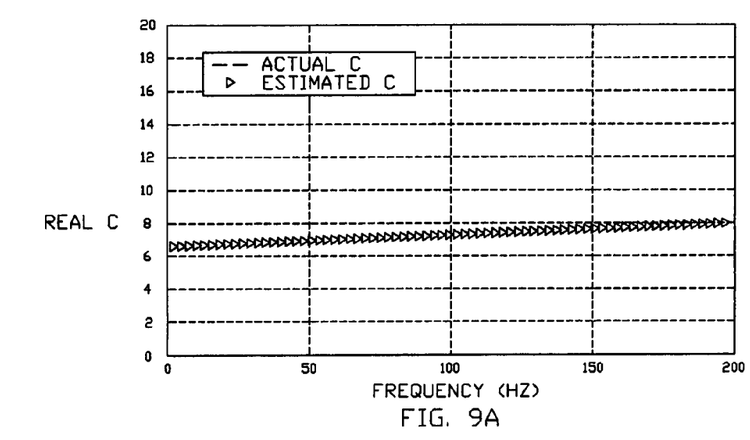
FIG. 9A is a plot of the real part of the wave propagation coefficient C versus frequency.
Figure 9B:
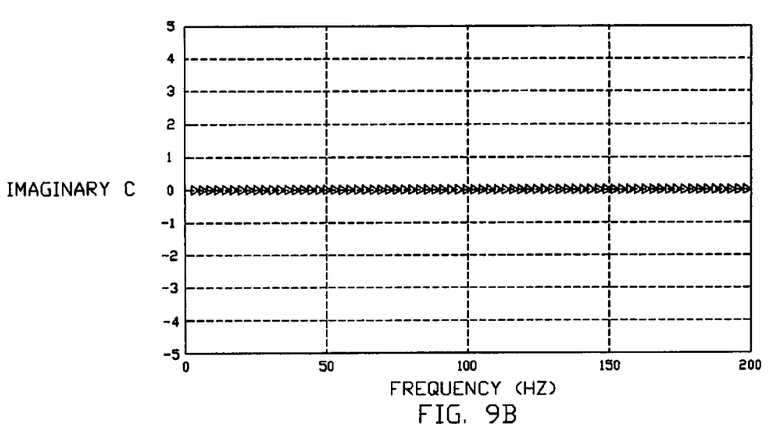
FIG. 9B is a plot of the imaginary part of the wave propagation coefficient C versus frequency.
Figure 10A:
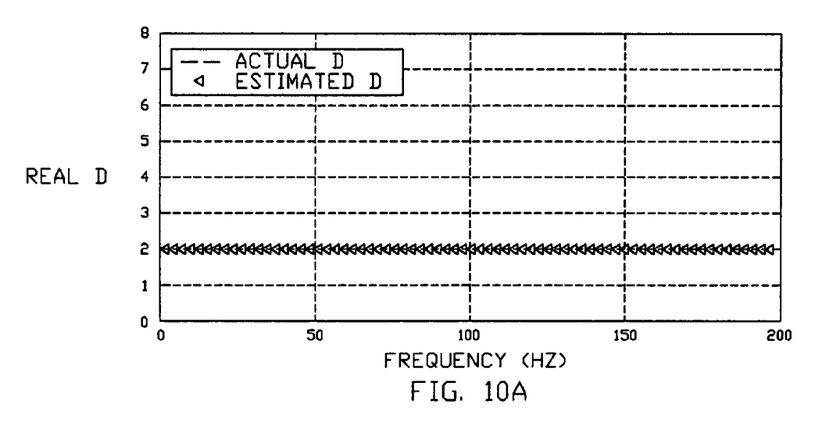
FIG. 10A is a plot of the real part of the wave propagation coefficient D versus frequency.
Figure 10B:
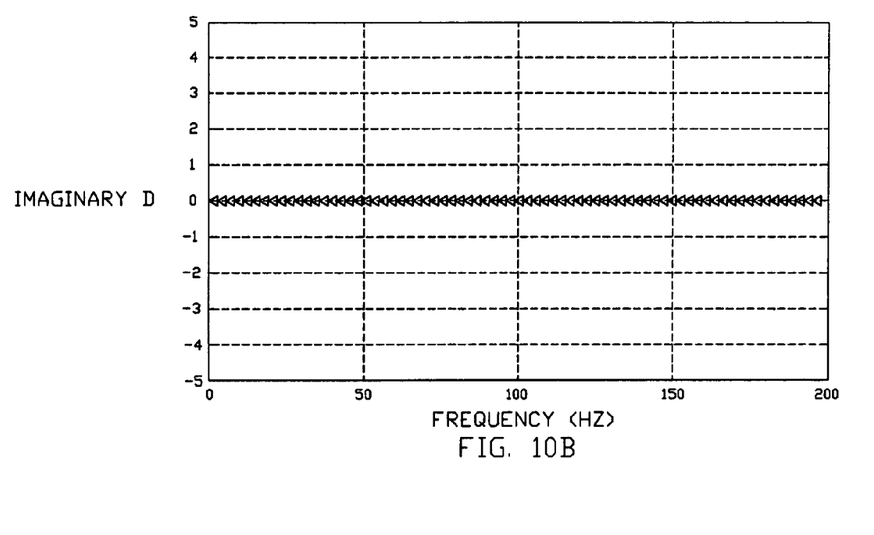
FIG. 10B is a plot of the imaginary part of the wave propagation coefficient D versus frequency.

Applying equations (34)–(41) to the functions $s_p$, $s_m$, and θ yields the estimated wavenumbers p and k. FIG. 5 is a plot of the wavenumbers versus frequency. The top plot is the real part and the bottom plot is the imaginary part of the wavenumbers. The actual wavenumber k used to formulate this problem is denoted with a solid line and the actual wavenumber p is marked with a dashed line. The estimated wavenumber k determined with equations (36), (37), (40), and (41) is denoted with "o" marks and the estimated wavenumber p determined with equations (34), (35), (38), and (39) is shown with square markers. FIG. 6 is a plot of wavespeeds versus frequency. The top plot is the real part and the bottom plot is the imaginary part of the wavespeeds. The actual wavespeed $c_1$ used to formulate this problem is denoted with a solid line and the actual wavespeed $c_2$ is marked with a dashed line. The estimated wavespeed $c_1$ determined with equation (42) is denoted with "o" marks and the estimated wavespeed $c_2$ determined with equation (43) is shown with square marks. FIGS. 7, 8, 9, and 10 are the wave propagation coefficients A, B, C, and D, respectively, versus frequency. The top plot is the real part and the bottom plot is the imaginary part of the wave propagation coefficients. In all four plots, the actual wave propagation coefficient is denoted with a dashed line and the estimated wave propagation coefficient is marked with triangle symbols.

TABLE 1

Value of n Versus Frequency

| Value of n | Minimum Frequency (Hz) | Maximum Frequency (Hz) |
|---|---|---|
| 0 | 0.0 | 96.6 |
| 1 | 96.6 | 193.0 |
| 2 | 193.0 | 200 |

TABLE 2

Value of m Versus Frequency

| Value of m | Minimum Frequency (Hz) | Maximum Frequency (Hz) |
|---|---|---|
| 0 | 0.0 | 42.6 |
| 1 | 42.6 | 85.2 |
| 2 | 85.2 | 127.9 |
| 3 | 127.9 | 170.3 |
| 4 | 170.3 | 200.0 |

In summary, the method comprises vibrating the structure in a manner that simultaneously excites a first wave and a second wave such that the first wave and the second wave comprise different types of wave motion. Seven measurements, such as accelerometer measurements are made in the structure at seven different positions in the structure. The seven measurements are set equal to seven frequency domain transfer functions. The seven frequency domain transfer functions are described in terms of six unknowns. The six unknowns comprise two unknowns related to a complex wavenumber for each of the first wave and the second wave and four unknowns related to four wave propagation coefficients for the first wave and the second wave. The complex wavenumber for each of the first wave and the second wave is determined utilizing the equations described herein. The complex wavespeed for the first wave and the second wave are determined from the complex wavenumber for each of the first wave and the second wave. Matrix techniques may be utilized to solve for the four unknowns related to the wave propagation coefficients for the first wave and the second wave.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method for characterizing system response of a structure, comprising:
    vibrating said structure in a manner that simultaneously excites a first wave and a second wave, said first wave and said second wave comprising different types of wave motion;
    making at least seven movement related measurements in said structure at seven different positions in said structure;
    setting said at least seven movement related measurements equal to seven frequency domain transfer functions, said seven frequency domain transfer functions being described in terms of six unknowns, said six unknowns comprising two unknowns related to a complex wavenumber for each of said first wave and said second wave, said six unknowns comprising four unknowns related to four wave propagation coefficients for said first wave and said second wave; and
    determining a complex wavenumber for each of said first wave and said second wave.

2. The method of claim 1, further comprising:
    determining a wavespeed for said first wave and said second wave from said complex wavenumber for each of said first wave and said second wave.

3. The method of claim 2, wherein said step of determining a wave speed comprises utilizing the following equations:

$$c_1(\omega) = \frac{\omega}{k(\omega)} \text{ and}$$

$$c_2(\omega) = \frac{\omega}{p(\omega)}$$

where:
$c_1$ is the complex wavespeed of said first wave,
$c_2$ is the complex wavespeed of said second wave,
w is the frequency of excitation
$k(\omega)$ is the complex wavenumber for said first wave, and
$p(\omega)$ is the complex wavenumber for said second wave.

4. The method of claim 1, wherein said at least seven movement related measurements each comprise a measurement at one of said seven positions divided by a common reference measurement.

5. The method of claim 3, further comprising utilizing accelerometer readings for said step of making seven movement related measurements.

6. The method of claim 4, wherein said step of setting said seven movement related measurements equal to seven frequency domain transfer functions comprises utilizing the following seven equations:

$$T_{-3} = \frac{U_{-3}(-3\delta, \omega)}{V_0(\omega)} = A\cos(3k\delta) - B\sin(3k\delta) + C\cos(3p\delta) - D\sin(3p\delta),$$

$$T_{-2} = \frac{U_{-2}(-2\delta, \omega)}{V_0(\omega)} = A\cos(2k\delta) - B\sin(2k\delta) + C\cos(2p\delta) - D\sin(2p\delta),$$

$$T_{-1} = \frac{U_{-1}(-\delta, \omega)}{V_0(\omega)} = A\cos(k\delta) - B\sin(k\delta) + C\cos(p\delta) - D\sin(p\delta),$$

$$T_0 = \frac{U_0(0, \omega)}{V_0(\omega)} = A + C,$$

$$T_1 = \frac{U_1(\delta, \omega)}{V_0(\omega)} = A\cos(k\delta) + B\sin(k\delta) + C\cos(p\delta) + D\sin(p\delta),$$

$$T_2 = \frac{U_2(2\delta, \omega)}{V_0(\omega)} = A\cos(2k\delta) + B\sin(2k\delta) + C\cos(2p\delta) + D\sin(2p\delta),$$

and $$T_3 = \frac{U_3(2\delta, \omega)}{V_0(\omega)} = A\cos(3k\delta) + B\sin(3k\delta) + C\cos(3p\delta) + D\sin(3p\delta),$$

where $\delta$ is the sensor to sensor separation distance (m), $V_0(\omega)$ is the reference measurement;
A, B, C, and D comprise said four unknowns related to four wave propagation coefficients for said first wave and said second wave; and
k and p comprise said two unknowns related to a complex wavenumber for each of said first wave and said second wave.

7. The method of claim 5, wherein said step of determining a complex wavenumber for each of said first wave and said second wave further comprises solving said seven equations utilizing the following equation:

$$\cos\left[\binom{k}{p}\delta\right] = \frac{-b \pm \sqrt{b^2 - 4ac}}{2a} = \phi,$$

where $\phi$ is typically a complex number and, $a = 4T_1^2 - 4T_{-1}^2 + 4T_{-2}T_0 - 4T_0T_2,$ $b = 2T_{-2}T_{-1} - 2T_{-2}T_1 + 2T_{-1}T_0 - 2T_0T_1 + 2T_{-1}T_2 - 2T_1T_2 + 2T_0T_3 - 2T_{-1}T_0,$ $c = T_{-1}^2 - T_1^2 + T_2^2 - T_{-2}^2 + T_{-3}T_{-1} - T_{-1}T_3 + T_{-3}T_1 - T_1T_3 + 2T_0T_2 - 2T_{-2}T_0.$ 8. The method of claim 6, wherein said step of determining a complex wavenumber for each of said first wave and said second wave further comprises,
    when the below equation is satisfied, $$(2j-1)\pi < \theta < (2j+1)\pi \quad j = 0, 2, 4, 6 \ldots \begin{cases} p = g \\ k = h \end{cases},$$

where j is a wrap counting integer, and $\theta = \text{angle}(b^2 - 4ac),$ then the solution to the real and imaginary parts of p is:

$$\text{Re}(p) = \begin{cases} \frac{1}{2\delta}\text{Arccos}(s_p) + \frac{m\pi}{2\delta} & n \text{ even} \\ \frac{1}{2\delta}\text{Arccos}(-s_p) + \frac{n\pi}{2\delta} & m \text{ odd} \end{cases},$$

$$\text{Im}(p) = \frac{1}{\delta}\log_e\left[\frac{\text{Re}(\phi_p)}{\cos[\text{Re}(p)\delta]} - \frac{\text{Im}(\phi_p)}{\sin[\text{Re}(p)\delta]}\right],$$

and the solution to the real and imaginary parts of k is:

$$\text{Re}(k) = \begin{cases} \frac{1}{2\delta}\text{Arccos}(s_m) + \frac{m\pi}{2\delta} & m \text{ even} \\ \frac{1}{2\delta}\text{Arccos}(-s_m) + \frac{m\pi}{2\delta} & m \text{ odd} \end{cases},$$

$$\text{Im}(k) = \frac{1}{\delta}\log_e\left[\frac{\text{Re}(\phi_m)}{\cos[\text{Re}(k)\delta]} - \frac{\text{Im}(\phi_m)}{\sin[\text{Re}(k)\delta]}\right].$$

where the value of m is determined from the function $s_m$, which is a periodically varying cosine function with respect to frequency and the value of n is determined from the function $s_p$, which is a periodically varying cosine function with respect to frequency.

9. The method of claim 7, wherein said step of determining a complex wavenumber for each of said first wave and said second wave further comprises,
when the below equation is satisfied, $$(2j-1)\pi < \theta < (2j+1)\pi \quad j = 1, 3, 5, 7 \ldots \begin{cases} p = h \\ k = g \end{cases},$$

then the solution to the real and imaginary parts of p are:

$$\text{Re}(p) = \begin{cases} \frac{1}{2\delta}\text{Arccos}(s_m) + \frac{m\pi}{2\delta} & n \text{ even} \\ \frac{1}{2\delta}\text{Arccos}(-s_m) + \frac{n\pi}{2\delta} & n \text{ odd} \end{cases},$$

$$\text{Im}(p) = \frac{1}{\delta}\log_e\left[\frac{\text{Re}(\phi_m)}{\cos[\text{Re}(p)\delta]} - \frac{\text{Im}(\phi_m)}{\sin[\text{Re}(p)\delta]}\right].$$

and the solution to the real and imaginary parts of k are:

$$\text{Re}(k) = \begin{cases} \frac{1}{2\delta}\text{Arccos}(s_m) + \frac{m\pi}{2\delta} & m \text{ even} \\ \frac{1}{2\delta}\text{Arccos}(-s_m) + \frac{m\pi}{2\delta} & m \text{ odd} \end{cases}.$$

$$\text{Im}(k) = \frac{1}{\delta}\log_e\left[\frac{\text{Re}(\phi_m)}{\cos[\text{Re}(k)\delta]} - \frac{\text{Im}(\phi_m)}{\sin[\text{Re}(k)\delta]}\right].$$

10. The method of claim 8 further comprising determining said four unknowns related to four wave propagation coefficients for said first wave and said second wave utilizing equation:

$$Ax = b \text{ where}$$

$$A = \begin{bmatrix} \cos(3k\delta) & -\sin(3k\delta) & \cos(3p\delta) & -\sin(3p\delta) \\ \cos(2k\delta) & -\sin(2k\delta) & \cos(2p\delta) & -\sin(2p\delta) \\ \cos(k\delta) & -\sin(k\delta) & \cos(p\delta) & -\sin(p\delta) \\ 1 & 0 & 1 & 0 \\ \cos(k\delta) & \sin(k\delta) & \cos(p\delta) & \sin(p\delta) \\ \cos(2k\delta) & \sin(2k\delta) & \cos(2p\delta) & \sin(2p\delta) \\ \cos(3k\delta) & \sin(3k\delta) & \cos(3p\delta) & \sin(3p\delta) \end{bmatrix},$$

$$x = \begin{bmatrix} A \\ B \\ C \\ D \end{bmatrix},$$

$$b = \begin{bmatrix} T_{-3} \\ T_{-2} \\ T_{-1} \\ T_0 \\ T_1 \\ T_2 \\ T_3 \end{bmatrix}.$$

and solving with $$x = (A^H A)^{-1} A^H b,$$

where the superscript H denotes complex conjugate transpose of the matrix.

* * * * *